United States Patent
Zermani

(10) Patent No.: US 6,764,653 B2
(45) Date of Patent: Jul. 20, 2004

(54) METHOD OF FORMING WELL(S) CONTAINING FILTRATION DEVICES

(75) Inventor: Thomas G. Zermani, Peabody, MA (US)

(73) Assignee: Millipore Corporation, Billerica, MA (US)

(*) Notice: Subject to any disclaimer, the term of this patent is extended or adjusted under 35 U.S.C. 154(b) by 0 days.

(21) Appl. No.: 10/120,107

(22) Filed: Apr. 11, 2002

(65) Prior Publication Data

US 2002/0108898 A1 Aug. 15, 2002

Related U.S. Application Data

(62) Division of application No. 09/834,584, filed on Apr. 13, 2001, now Pat. No. 6,514,463, which is a division of application No. 09/305,696, filed on May 5, 1999, now Pat. No. 6,309,605.

(51) Int. Cl.[7] ............................................. B01D 29/00
(52) U.S. Cl. .................. 422/101; 210/451; 210/455; 422/102; 422/104; 156/309.9; 156/322
(58) Field of Search .................... 210/451, 455, 210/473, 477; 422/101, 102, 104; 156/309.9, 322

(56) References Cited

U.S. PATENT DOCUMENTS

| | | | | |
|---|---|---|---|---|
| 4,154,795 A | * | 5/1979 | Thorne | 422/99 |
| 4,976,926 A | * | 12/1990 | Matkovich | 422/101 |
| 5,028,328 A | * | 7/1991 | Long | 210/477 |
| 5,108,704 A | * | 4/1992 | Bowers et al. | 422/70 |
| 5,116,496 A | * | 5/1992 | Scott | 210/232 |

* cited by examiner

Primary Examiner—John Kim
(74) Attorney, Agent, or Firm—John Dana Hubbard

(57) ABSTRACT

A single or multiwell plate using membrane, preferably an ultrafiltration membrane to filter selected solutes from a liquid is disclosed. In particular, a preferred construction and method of sealing the membrane to the interior of the well so as to form an integral seal between the top portion of the well and the bottom portion is disclosed. The preferred method is to use a heat seal device which secures the filter to the underdrain portion of the device.

7 Claims, 3 Drawing Sheets

METHOD OF FORMING WELL(S) CONTAINING FILTRATION DEVICES

This application is a divisional application of U.S. Ser. No. 09/834,584 filed Apr. 13, 2001, now U.S. Pat. No. 6,514,463, which is a divisional of U.S. Ser. No. 09/305,696, filed May 5, 1999, now U.S. Pat. No. 6,309,605 B1.

The present invention relates to a single or multi-well filtration device suitable for the concentration or assay of biological and biochemical materials. The present invention more particularly relates to a singl or multi-well filtration device having the filtration media sealed to the underdrain of the device.

BACKGROUND OF THE INVENTION

Test plates having one or more individual wells or reaction chambers are common laboratory tools. Such devices are employed for a wide variety of purposes and assays, see U.S. Pat. No. 4,902,481. Single welled devices are also well known, see U.S. Pat. Nos. 3,483,768, 4,632,761 and 4,722,792.

The plate filtration devices include two plates, the upper plate, commonly referred to as the well plate and a lower plate, commonly referred to as the underdrain. The well plate contains one or more individual wells that are open at one end and have a filtration membrane sealed across the opposite end. The underdrain is provided with a second set of individual well(s), which register with the wells of the well plate. Each of the wells in the underdrain have an open end and a second end which contains a small opening having a spout which opening and spout are designed to receive liquid which passes through the filtration membrane of the upper plate. The size of the opening and the spout are controlled so that liquid is retained in the well plate above the membrane under normal atmospheric conditions due to surface tension forces but passes through the membrane and the opening and spout when a pressure differential is applied across the membrane.

The filtration media has been secured to the lower portion of the well plate in several ways. In one method, a sheet of filtration membrane is stretch across the bottom of the well plate and adhered to each of the individual well or wells. In a second method, individual membrane pieces are cut and placed within the interior of the well where either friction or an undercut is used to maintain the position of the membrane in the well. In a third common method, the individual pieces are adhered to the bottom portion of the individual wells of the well plate.

The first method has problems in that liquid that passes through the membrane can travel laterally between wells and contaminate adjacent wells. The second method relies upon proper placement and maintenance of that placement in the well over time. Vibration, rough handling and other factors can displace the membrane causing loss of the sample or at least a portion of the sample or liquid within the sample. Additionally, it fails to form an integral seal such that liquid may bypass the filter altogether resulting in loss of product and contamination of the filtrate. The third method has been the preferred and most commonly used method as it ensures that there is no cross talk or contamination between the wells and there is a true seal of the membrane to the well plate so as to prevent leakage.

In these devices, the membrane has been limited to microporous membrane or a glass fiber depth filter or other coarse filtration media. This is due to the nature of the membrane and its ability to be sealed to the bottom of the well in the well plate. Other membranes, in particular ultrafiltration (UF) membranes are mentioned as being of possible use, however they have not been successfully sealed within the well plate. This is due to the structure and composition of the UF membranes. These membranes are relatively thin and fragile. Therefore these membranes are typically cast upon a support structure such as a non-woven porous sheet or a microporous membrane. The UF membrane itself is a relatively thin, dense material which is extremely sensitive to any type of mechanical or chemical bonding method.

What is desired is a plate system which allows for the use of membranes other than microporous membranes and which contains all of the advantages of the prior plates, namely avoiding lateral flow and contamination between the wells and the use of multiple wells in the same device. The present invention provides such a device.

SUMMARY OF THE INVENTION

The present invention provides an improved single or multi-well filtration apparatus that permits the use of membranes other than microporous membranes, in particular UF membranes, nanofiltration membranes and reverse osmosis membranes. Additionally, the present invention provides such a device that is capable of having liquid removed from each well by filtration with a vacuum or under pressure including by centrifugal forces. The filtrate from each well is recovered separately from the filtrate in adjacent wells. Thus, this apparatus permits the recovery and/or analysis of the retentate and/or filtrate without cross contamination between the adjacent wells.

The present invention has a well plate having both ends open and an underdrain that has one end (the lower end) essentially closed except for a small opening and spout. The other end of the underdrain has a filtration membrane sealed across the well such that any liquid will be retained in the well of the well plate until either a vacuum or positive pressure is applied to filter the liquid through the membrane. The membrane is sealed to the well of the underdrain by any conventional method such as heat bonding, ultrasonic bonding, vibrational bonding, friction bonding, adhesive bonding, solvent bonding or overmolding. It is preferred that the membrane be sealed to the underdrain by heat bonding.

It is a preferred object of the present invention to provide a filtration device having an underdrain portion having one or more individual drain compartments, each of said one or more compartments having a drain opening and a drain compartment wall located adjacent the outer periphery of each compartment; one or more filter components located din in one or more of the drain compartments contained in the underdrain portion, each of said filter components being attached to the underdrain portion in a manner to form in integral seal between the periphery of the filter component and a drain compartment of the underdrain portion; and a well plate having one or more individual wells, said plurality of wells being arranged in number and location so as to register with the underdrain portion.

It is another preferred object of the present invention to provide a multiple well device having an underdrain portion having a plurality of individual drain compartments, each of said compartments having a drain opening formed in the lower portion of the compartment and a drain compartment wall located adjacent the outer periphery of the compartment; a plurality of filter components contained in at least a portion of the compartments of the underdrain portion, each of said filter components being attached to the underdrain portion so as to form an integral seal between the periphery of the filter component and the compartment of the underdrain portion; and a well plate having a plurality of individual wells, said plurality of wells being arranged in a number and location so as to register with the underdrain portion when said well plate is placed onto of the underdrain portion.

It is a further preferred object of the present invention to provide a method of forming a multiple well filtration device by forming an underdrain portion, said underdrain portion having a plurality of individual drain compartments, said compartments having a drain opening, a filter support surrounding said drain opening and a drain compartment wall located adjacent the outer periphery of the filter support; placing a filter component in each of the drain compartments contained in the underdrain portion, attaching the filter component in each of said drain compartments at the periphery of the filter component to the drain compartment in a manner to form in integral seal between the periphery of the filter component and a drain compartment of the underdrain portion; forming a well plate having a plurality of individual wells, said plurality of wells being equal in number and location with the number and location of the plurality of drain compartments in the underdrain portion; and securing the well plate to the underdrain portion so as to form a plurality of sealed well filtration devices, each having a well, a drain and a filter sealed in between.

It is a further preferred object of the present invention to provide a filtration apparatus formed of a first plate having at least one first well, each of said at least one first wells having a first open end and a second open end and an outside peripheral surface, a second plate having at least one second well having a first open end, a first closed end, said closed end having a hole extending through the closed end thickness and an inside peripheral surface, said second plate being secured to said first plate so as to form a continuous well between the top of the first plate and the first closed end of the second plate, a filter positioned between said second end of said first plate and said first closed end of said second plate and an open spout having an open end, said spout being in fluid communication with said hole.

These and other embodiments and objects of the present invention will be made clear from the following description and claims.

IN THE DRAWINGS

DETAILED DESCRIPTION OF THE INVENTION

Figure 1:
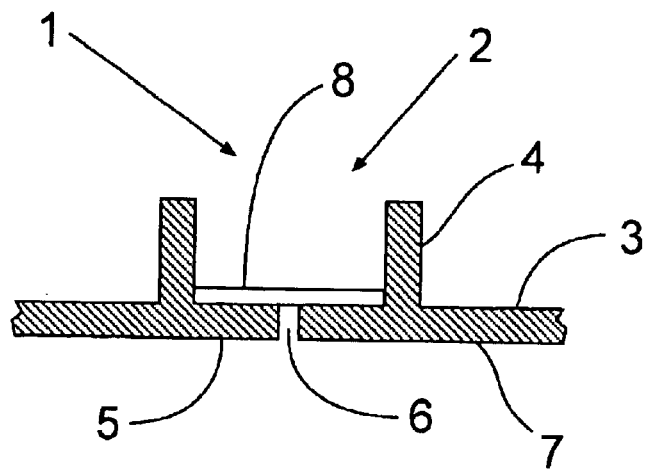
FIG. 1 shows a first embodiment of the present invention in cross sectional view.
Figure 2:
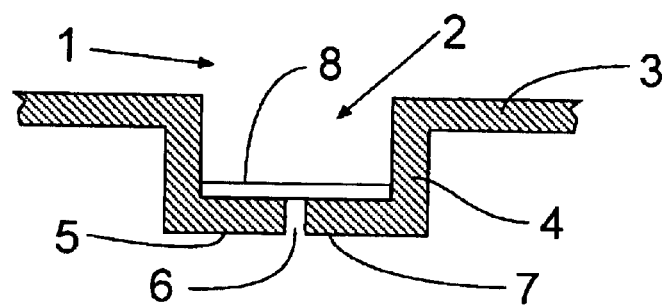
FIG. 2 shows a second embodiment of the present invention in cross sectional view.

In FIG. 1 is shown a first embodiment of the present invention. In this embodiment the device is formed of a single plate 1. This plate 1 has one or more wells 2. In the embodiment as shown the one or more wells rise up from a planar portion 3. Alternatively as shown in FIG. 2, the wells may depend downwardly from the planar portion 3. The inner wall 4 of the one or more wells forms the wells themselves. The wells are closed at the bottom 5. An opening 6 is formed in the bottom of the wells to as to form a fluid communication between the inner surface of the bottom 5 of the well and the exterior surface 7 of the bottom 5. A filter 8 is contained in the well as shown in FIGS. 1 and 2 adjacent the bottom 5. The filter is sealed to the inner surface of the well so as to separate the opening 6 from the rest of the well. This sets up a fluid tight seal between the two well portions such that all fluid that is to pass through the opening 6 must first pass through the filter 8.

Figure 3:
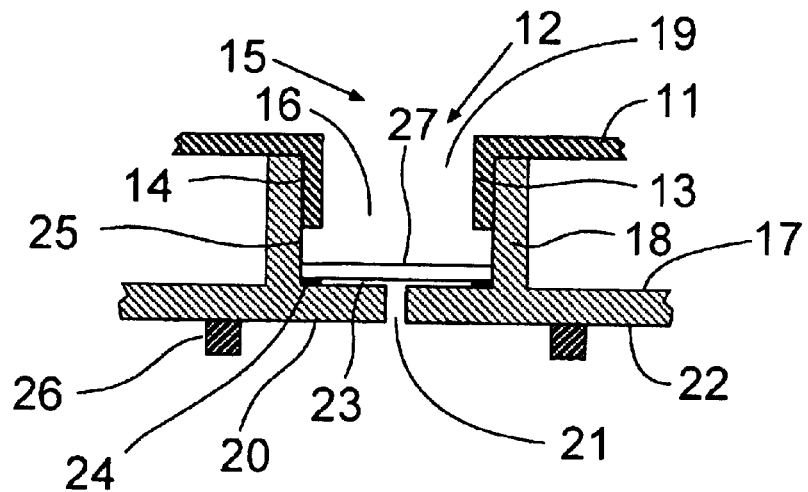
FIG. 3 shows a third embodiment of the present invention in cross sectional view.

Referring to FIG. 3, a filtration device according to a second embodiment of the invention is shown. The device shows a first plate 11 having at least one well 12. The well 12 has an inner peripheral wall 13 and an outer peripheral wall 14. The top and the bottom of the well, 15 and 16, are open. The second plate 17 has at least one well 18 having a first opened end 19 and a second closed end 20. The second closed end 20 has an opening 21 that passes from the interior of the well 18 to the exterior of the well 22. The inner surface of the second closed end 20 may have a filter support 23 which extends across a significant portion of the closed end 20 leaving a raised periphery 24 adjacent the inner wall 25 of the well 18 as shown in the Figure. Alternatively, no filter support 23 may be used and the inner surface of the second closed end may be substantially planar (not shown). Optionally as shown, the second plate 17 may have a collar 26 which surrounds each opening 21 of each well 18 in order to prevent any fluid from one well from entering or mixing with the fluid of an adjacent well. A filter 27 is secured within the well 18 about its periphery to the raised periphery 24 of the closed end 20. In those embodiments which use no filter support or raised periphery, the filter is simply secured adjacent the bottom of the closed end. The filter 27 is secured to the periphery 24, if used or adjacent the bottom of the closed end, if not used, such that it forms a liquid type seal between the filter 27 and the area of the bottom of the closed end adjacent the opening of the well such that all liquid must flow through the filter before entering the opening.

As shown, the first plate 11 is secured to the second plate 17. These plates 11 and 17 may be secured by a snap or press fit between the wells of the two plates which allow the frictional forces between the inner surface of one well and the outer surface of the other well to hold the two plates together. As shown, the outer surface of the first plate well is secured to the inner surface of the second plate well. Alternatively, the outer surface of the second plate well may be secured to the inner surface of the first plate well. Additionally, rather than using a snap or press fit to form a removable secure fit between the plates, one may use a thermal bond or adhesive bond to permanently secure the two plates together. In an additional embodiment of the present invention, the first and second plates are secured together by an overmolding or injection molding process. The method by which the two plates are secured is a matter of choice to the practitioner.

Figure 4:
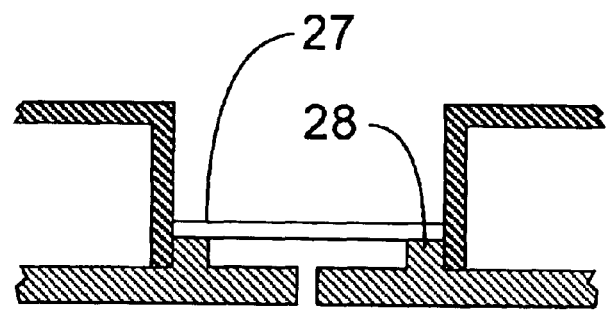
FIG. 4 shows another embodiment of the present invention in cross sectional view.
Figure 5:
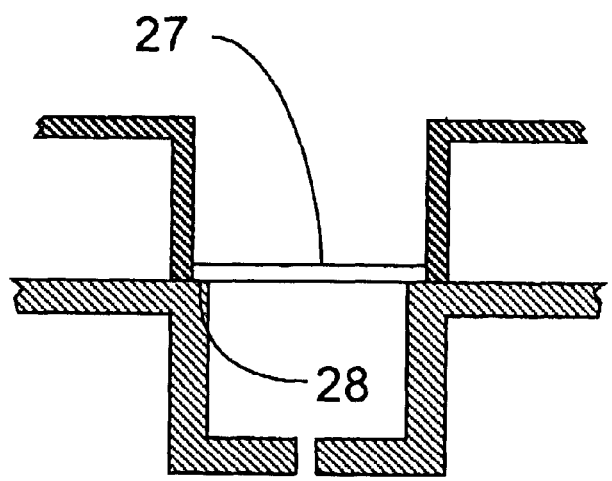
FIG. 5 shows a further embodiment of the present invention in cross sectional view.

FIGS. 4 and 5 show an alternative filter arrangement for the embodiment of FIG. 3. In these embodiments, the filter 27 rather than being sealed adjacent the bottom of the well of the second plate is secured adjacent the top 28 of the well of the second plate. In this embodiment it is preferable, although not necessary that the well of the second plate be of a depth less than that of the first plate. When assembled the well is formed between the two plates and the filter is still sealed above the opening and still causes all liquid to flow through the filter before entering the opening.

These embodiments allow for simpler manufacturing as a sheet of filter material may be laid across the upper surface of the second plate and sealed adjacent to the periphery of the inner well wall of the second plate. Excess filter material is then removed leaving discrete isolated filters at each well of the second plate, which are incapable of any crosstalk or contamination. Alternatively, one may still use individual filter pieces and secure them to the area adjacent to the inner wall of the well of the second plate.

In a further embodiment (not shown) one may use more than one filter in a single well. Typically, these filters are arranged on top of each other. Only the bottom most filter needs to be sealed in a fluid type arrangement with the compartment. Preferably all filters are sealed so as to ensure complete filtration. Alternatively, some wells may contain no filter element at all. One may also vary the filters used between the various wells so that one may obtain a series of different filter elements within the same multiple well device.

Suitable polymers which can be used to form the underdrain and if used the well plate include but are not limited to polycarbonates, polyesters, nylons, PTFE resins and other fluoropolymers, acrylic and methacrylic resins and copolymers, polysulphones, polyethersulphones, polyarylsulphones, polystryenes, polyvinyl chlorides, chlorinated polyvinyl chlorides, ABS and its alloys and blends, polyolefins, preferably polyethylenes such as linear low density polyethylene, low density polyethylene, high density polyethylene, and ultrahigh molecular weight polyethylene and copolymers thereof, polypropylene and copolymers thereof and metallocene generated polyolefins. Preferred polymers are polyolefins, in particular polyethylenes and their copolymers, polystyrenes and polycarbonates. When an underdrain and well plate are used in combination they may be made of the same polymer or different polymers as desired. Likewise the polymers may be clear or rendered optically opaque or light impermeable. When using opaque or light impermeable polymers, it is preferred that their use be limited to the side walls so that one may use optical scanners or readers on the bottom portion to read various characteristics of the retentate. When the filter is heat bonded to the underdrain, it is preferred to use polyolefins due to their relatively low melting point and ability to form a good seal between the device and the filter.

The filter may be of any variety commonly used in filtering biological specimens including but not limited to microporous membranes, ultrafiltration membranes, nanofiltration membranes, or reverse osmosis membranes. Preferably microporous membranes, ultrafiltration membranes or nanofiltration membranes are used. Even more preferably, ultrafiltration membranes are used.

Representative suitable microporous membranes include nitrocellulose, cellulose acetate, polysulphones including polyethersulphone and polyarylsulphones, polyvinylidene fluoride, polyolefins such as ultrahigh molecular weight polyethylene, low density polyethylene and polypropylene, nylon and other polyamides, PTFE, thermoplastic fluorinated polymers such as poly (TFE-co-PFAVE), polycarbonates or particle filled membranes such as EMPORE® membranes available from 3M of Minneapolis, Minn. Such membranes are well known in the art (add Millipore patent numbers) and are commercially available from a variety of sources including Millipore Corporation of Bedford, Mass. If desired these membranes may have been treated to render them hydrophilic. Such techniques are well known and include but are not limited to grafting, crosslinking or simply polymerizing hydrophilic materials or coatings to the surfaces of the membranes.

Representative ultrafiltration or nanofiltration membranes include polysulphones, including polyethersulphone and polyarylsulphones, polyvinylidene fluoride, and cellulose. These membranes typically include a support layer that is generally formed of a highly porous structure. Typical materials for these support layers include various non-woven materials such as spun bounded polyethylene or polypropylene, or glass or microporous materials formed of the same or different polymer as the membrane itself. Such membranes are well known in the art, and are commercially available from a variety of sources such as Millipore Corporation of Bedford, Mass.

As described above, while one well in each plate can be used; it is envisioned that a plurality of wells will be used. When a plurality of wells are used, it is important that the wells of the first plate register with the wells of the second plate. Typically multiple well plates have been made in formats containing 6, 96, 384 or up to 1536 wells and above. The number of wells used is not critical to the invention. This invention may be used with any multiple number of wells provided that the filter is capable of being secured to the second plate in a manner which forms a liquid tight seal between the periphery of the filter and the inner surface of the closed end of the wells of the second plate. The wells are typically arranged in mutually perpendicular rows. For example, a 96 well plate will have 8 rows of 12 wells. Each of the 8 rows is parallel and spaced apart from each other. Likewise, each of the 12 wells in a row is spaced apart from each other and is in parallel with the wells in the adjacent rows. A plate containing 1536 wells typically has 128 rows of 192 wells.

A variety of methods for forming a device according to the present invention may be used. Any method which seals the membrane within the well of the plate (in the single plate design) and in the well of the bottom plate (in the two plate design) such that all fluid within the well must pass through the filter before leaving the well through the bottom opening will be useful in this invention.

Figure 6:
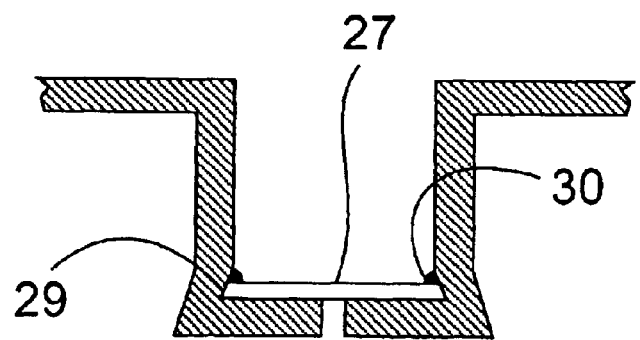
FIG. 6 shows an additional embodiment of the present invention in cross sectional view.

One method of forming such a device is to form a single plate of a suitable plastic as described above and use a mechanical seal between the well wall and the filter. Such a device is shown in FIG. 6. In this embodiment, there is a undercut formed around the periphery of the inner wall of the well. The filter is sized so as to fit within the undercut portion of the well. The filter is placed within the well as shown in FIG. 6. Optionally, as shown in the figure, a sealing gasket is applied on top of the filter within the undercut. This sealing gasket applies pressure to the filter and ensures that all the fluid must pass through the filter thereby eliminating any leakage or bypass of the filter by the fluid. As shown, this gasket may be in the form of a preformed gasket such as an O-ring. Alternatively, a gasket formed of a molten or liquid material may be cast into the undercut to seal the filter in place. An example of a molten material suitable for this embodiment, are any of the well-known hot melt materials such as polyethylene or polypropylene or ethylene vinyl acetate copolymers. A liquid gasket may be formed of any curable rubber or polymer such as an epoxy, urethane or synthetic rubber.

Another method of forming such a device is to use an adhesive to bond and seal the edge of the filter within the well such as all fluid must pass through the filter before entering the opening in the bottom of the well. Adhesive may be either molten or curable as discussed above.

A further method is to use a thermal bond to secure the filter to the well. In this embodiment, a filter sealing device which has a sealing surface which is heated is brought into contact with the upper filter surface and transfer its thermal energy to the surrounding filter and well material. The energy causes either the filter material or the well materials or both to soften and or melt and fuse together forming an integral, fluid tight seal. This process may be used when either the filter material or the well material or both are formed of a thermoplastic material. It is preferred that the well as well as at least a portion of the filter material adjacent the downstream side of the filter be formed of a thermoplastic material. The sealing surface is only a portion of the filter surface and is a continuous structure so that a ring or peripheral area of the filter is sealed to the well so as to form a liquid fight seal between the filter, well and the opening in the bottom of the well.

Figure 7:
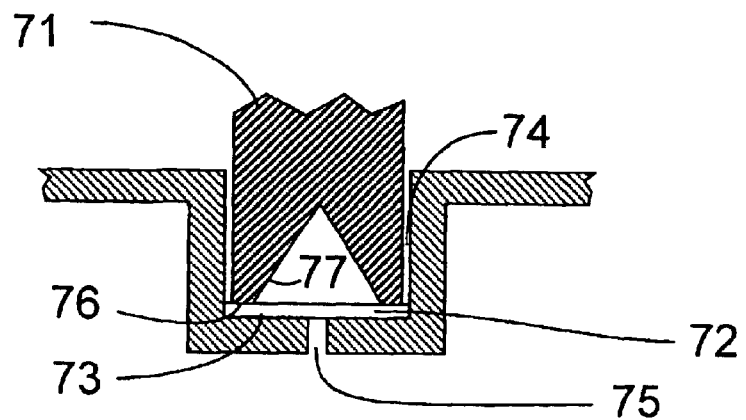
FIG. 7 shows a first method and device for sealing the membrane into the device of the present invention in cross sectional view.

FIG. 7 shows one such sealing device 71 in the process of sealing a filter 72 to a portion of the well 73 such that all fluid communication between the well 74 and the opening 75 in the bottom of the well 74 is through the filter 72. The sealing device 71, as shown has a sealing surface 76 spaced radially outward from the center of the device diameter and is the lowermost projection of the device. The remainder of the area of the sealing device lowermost face 77 is recessed in order to avoid contact with the filter 72. The sealing surface 76 is brought into contact with the surface of a filter 72 contained within the well 74. Thermal energy is transferred from the sealing device 71 to the area of filter below the sealing surface 76. This causes either the portion of the filter and/or the well below that surface to absorb the thermal energy causing it to soften or melt. As the filter is porous, a portion of the filter beneath the sealing surface collapses and is rendered non-porous as well as thermally bonding to the well portion below it. In this manner, a fluid tight seal is formed between the membrane and the well around the periphery of the opening in the bottom of the well.

Figure 8:
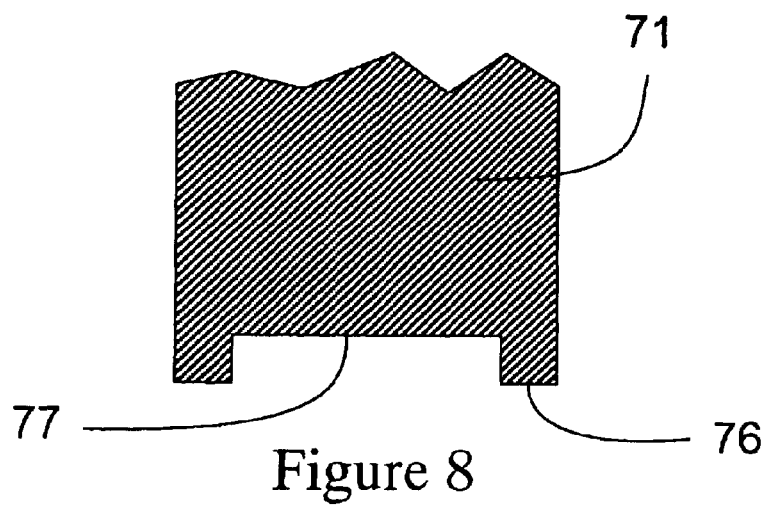
FIG. 8 shows a first embodiment of the sealing device of the present invention in cross sectional view.

As shown, the remainder of the face 77 of the sealing device 71 is tapered inwardly as a conical depression. Alternatively, the inner portion could be relatively flat leaving an outer peripheral ring as shown in FIG. 8 or any other design which accomplishes the same effect. Additionally, the sealing surface 76 does not need to be the outermost portion of the heat-sealing device 71 as is shown in FIG. 7. It may be positioned inward from the outer edge of the device. The position is not critical so long as an adequate seal and sufficient active filter area is maintained.

Figure 9:
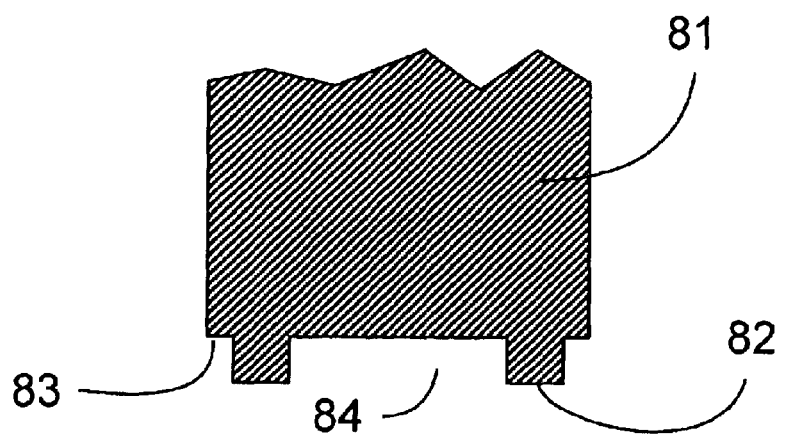
FIG. 9 shows an alternative embodiment of the sealing device of the present invention in cross sectional view.

FIG. 9 shows such an embodiment. Here the sealing device 81 has the outer periphery 82 stepped inward of outer edge 83 of the device 81. In this embodiment, both the surface along the outer edge 83 outside the sealing periphery as well as that surface 84 inside the sealing periphery is recessed such that only the sealing periphery contacts the filter.

The sealing device is preferably formed of a highly thermally conductive material such as metal including but not limited to stainless steel, aluminum, copper or titanium. Preferably, metal/polymer heaters such as silicone faced heaters may be used. Optionally, the metal may be coated with a material such as PTFE resin to avoid any sticking between the device and the filter after sealing.

Any method may be used to heat the sealing device. Typical methods include electrical resistance heaters, radiant heaters and steam or other high temperature liquid heaters which transfer their thermal energy to the sealing device. The heaters used are not critical so long as they provide adequate thermal energy to the filter and/or well so long as a thermal bond between the filter and the well is formed.

The temperature used to create the thermal bond is dependent upon the materials used for the filter and the well. It should be of a sufficient temperature so as to cause a thermal softening or melting of one or the other or both of these components so that a thermal bond which forms a fluid fight seal is accomplished. Preferably, the temperature selected also does not cause damage to either the membrane or well adjacent the area below the sealing surface. In this way, only a select portion of the membrane and well are sealed to each other allowing the remainder of the filter inside the seal to function normally and preventing any destruction or distortion of the well. With the types of filters discussed above and the plastics typically used for making welled devices of the type envisioned by the present invention, the temperature of the well/filter should be in a range from about 250° F. to about 700° F. (about 121° C. to about 371° C.). More preferably, it is in a range of from about 350° F. to about 600° F. (about 177° C. to about 315° C.) and most preferably from about 400° F. to about 600° F. (204 to about 315° C.).

The sealing device should be designed such that it fits within the well of the device and can be easily removed. Preferably its outer diameter is slightly smaller than that of the inner wall diameter of the well. Most wells are circular in design and the sealing device may also be of a circular design. However, the design of the device is not so limited so long as it fits within the well and forms a complete liquid tight seal around a portion of the filter. For example, polygonal shapes such as triangles, squares, hexagons and other such shapes may be used. Likewise, the well design need not be circular. It too may be a polygonal shape if desired.

This is the preferred method of sealing the filter in the well of the present invention. It is especially preferred with ultrafiltration membranes. As discussed above, ultrafiltration membranes are relatively thin and fragile material and typically are cast or laminated to a support layer to give it strength and protect its integrity. Such membranes are typically sensitive to heat and dryness that often collapse the pores of the structure rendering it non-porous. These membranes usually contain one or more humectants such as one or more glycols that prevent the membrane from drying and thus keeps the pores in the ultrafiltration membrane from collapsing. Both of these limitations have made the sealing of an ultrafiltration membrane extremely difficult. The humectants tend to prevent adequate sealing of the filter to a surface. The heat, especially in small area devices such as multiple well plates tended to cause the collapse of a significant area of membrane which led to a dramatic reduction in active filter area. It has been found that this thermal bonding method will provide an adequate fluid tight seal between the membrane and the well despite the existence of humectants such as glycols and without the collapse of the portion of the ultrafiltration membrane adjacent the seal.

EXAMPLE

A polyethylene underdrain plate of a 96 well plate known as the Multiscreen® device available from Millipore Corporation was obtained. The wells had an inner diameter of 0.300 inches. A series of filter elements formed from a cellulosic material commercially available as YMF 30 membrane from Millipore Corporation were made of a diameter substantially equal to but slightly less than the inside diameter of the wells of the underdrain (about 0.290 inches).

The filter elements were placed within the wells of the underdrain. A thermal sealing device identical of the configuration of FIG. 7, having a sealing surface with an inner diameter of 0.235 inches and an outer diameter of 0.265 inches made of aluminum coated with PTFE resin and being heated by an electrical resistance heater was inserted into each well with sufficient pressure to slightly compress the membrane. The sealing device was heated to a temperature of about 460° F. for a period of 2 seconds. The thermal energy was then ceased and the sealing device removed from the well. A fluid tight seal was formed between the filter and the well surface as evidenced by a BSA test. The porosity of the remainder of the filter was also confirmed by the same BSA test.

What is claimed is:

1. A method of forming a multiple well filtration device comprising the steps of:

forming an underdrain portion, said underdrain portion having a plurality of individual drain compartments, each compartment having an open top and a closed bottom, said compartments having one or more drain openings formed in the bottom portion and a drain compartment wall located adjacent an outer periphery of the closed bottom;

placing a filter component in each of the drain compartments contained in the underdrain portion, bonding the filter component in each of said drain compartments at the periphery of the filter component to the drain compartment in a manner to form in integral seal between the periphery of the filter component and a drain compartment of the underdrain portion wherein the filter component is formed of an ultrafiltration membrane having a porous bottom support layer and an ultraporous upper layer, the bottom layer and upper layer being integrally attached to each other and wherein the periphery of the filter component is bonded to the drain compartment of the underdrain portion so as to form an integral seal between the periphery of the filter component and the drain compartment.

2. The method of claim 1 further comprising forming a well plate having a plurality of individual wells, said plurality of wells being in number and location so as to align and register with the drain compartments in the underdrain portion; and securing the well plate to the underdrain portion so as to form a plurality of sealed well filtration devices, each having a well, a drain and a filter sealed in between.

3. A method of forming a multiple well filtration device comprising the steps of:

forming an underdrain portion, said underdrain portion having a plurality or individual drain compartments, each compartment having an open top and a closed bottom, said compartments having one or more drain openings formed in the bottom portion and a drain compartment wall located adjacent an outer periphery of the closed bottom;

placing a filter component in each of the drain compartments contained in the underdrain portion, bonding the filter component in each of said drain compartments at the periphery of the filter component to the drain compartment in a manner to form in integral seal between the periphery of the filter component and a drain compartment of the underdrain portion wherein the filter component is formed of an ultrafiltration membrane having a porous bottom support layer and an ultraporous upper layer, the bottom layer and upper layer being integrally attached to each other and the attaching between the filter component and the drain compartment is by heat bonding of the bottom support layer of the ultrafiltration membrane and the drain compartment.

4. A method of forming a multiple well filtration device comprising the steps of:

forming an underdrain portion, said underdrain portion having a plurality of individual drain compartments, each compartment having an open top and a closed bottom, said compartments having one or more drain openings formed in the bottom portion and a drain compartment wall located adjacent an outer periphery of the closed bottom;

placing a filter component in each of the drain compartments contained in the underdrain portion, bonding the filter component in each of said drain compartments at the periphery of the filter component to the drain compartment in a manner to form in integral seal between the periphery of the filter component and a drain compartment of the underdrain portion wherein the filter component is formed of an ultrafiltration membrane having a porous bottom support layer and an ultraporous upper layer, the bottom layer and upper layer being integrally attached to each other and the attaching between the filter component and the drain compartment is by heat bonding of the bottom support layer of the ultrafiltration membrane and the drain compartment and wherein at least a portion of the multiple well device is formed of a light impermeable material.

5. A method of forming a multiple well filtration device comprising the steps of:

forming an underdrain portion, said underdrain portion having a plurality of individual drain compartments, each compartment having an open top and a closed bottom, said compartments having one or more drain openings formed in the bottom portion and a drain compartment wall located adjacent an outer periphery of the closed bottom;

placing a filter component in each of the drain compartments contained in the underdrain portion, bonding the filter component in each of said drain compartments at the periphery of the filter component to the drain compartment in a manner to form in integral seal between the periphery of the filter component and a drain compartment of the underdrain portion and wherein the filter component is formed of an ultrafiltration membrane having a porous bottom support layer and an ultraporous upper layer and wherein the periphery of the filter component is bonded to the drain compartment of the underdrain portion by a heat bonding at a temperature range from about 121° C. to about 371° C. so as to form an integral seal between the periphery of the filter component and the drain compartment.

6. A method of forming a multiple well filtration device comprising the steps of:

forming an underdrain portion, said underdrain portion having a plurality of individual drain compartments, each compartment having an open top and a closed bottom, said compartments having one or more drain openings formed in the bottom portion and a drain compartment wall located adjacent an outer periphery of the closed bottom;

placing a filter component in each of the drain compartments contained in the underdrain portion, bonding the filter component in each of said drain compartments at the periphery of the filter component to the drain compartment in a manner to form in integral seal between the periphery of the filter component and a drain compartment of the underdrain portion wherein the filter component is formed of an ultrafiltration membrane having a porous bottom support layer and an ultraporous upper layer and wherein the periphery of the filter component is bonded to the drain compartment of the underdrain portion by a heat bonding and the heat bonding temperature is from about 177° C. to about 315° C.

7. A method of forming a multiple well filtration device comprising the steps of:

forming an underdrain portion, said underdrain portion having a plurality of individual drain compartments, each compartment having an open top and a closed bottom, said compartments having one or more drain openings formed in the bottom portion and a drain compartment wall located adjacent an outer periphery of the closed bottom;

placing a filter component in each of the drain compartments contained in the underdrain portion, bonding the filter component in each of said drain compartments at the periphery of the filter component to the drain compartment in a manner to form in integral seal between the periphery of the filter component and a drain compartment of the underdrain portion wherein the filter component is formed of an ultrafiltration membrane having a porous bottom support layer and an ultraporous upper layer and wherein the periphery of the filter component is bonded to the drain compartment of the underdrain portion by a heat bonding and further comprising forming a well plate having a plurality of individual wells, said plurality of wells being in number and location so as to align and register with the drain compartments in the underdrain portion; and securing the well plate to the underdrain portion so as to form a plurality of sealed well filtration devices, each having a well, a drain and a filter sealed in between.

* * * * *